US008444337B2

(12) United States Patent
Teller

(10) Patent No.: US 8,444,337 B2
(45) Date of Patent: May 21, 2013

(54) LIP BALM WITH SPHERICAL SURFACE AND METHOD FOR PRODUCING

(75) Inventor: Jonathan Teller, New York, NY (US)

(73) Assignee: The Kind Group, New York, NY (US)

( * ) Notice: Subject to any disclaimer, the term of this patent is extended or adjusted under 35 U.S.C. 154(b) by 533 days.

(21) Appl. No.: 12/632,114

(22) Filed: Dec. 7, 2009

(65) Prior Publication Data

US 2011/0135377 A1    Jun. 9, 2011

(51) Int. Cl.
*A45D 40/20* (2006.01)
(52) U.S. Cl.
USPC .............................. 401/88; 401/98; 206/385
(58) Field of Classification Search
USPC ......... 401/49, 88, 98; 206/385, 457; 132/305; 220/4.21, 4.24, 4.25, 654, 651
See application file for complete search history.

(56) References Cited

U.S. PATENT DOCUMENTS

| | | | |
|---|---|---|---|
| 75,524 A | 3/1868 | Chase | |
| 1,852,455 A * | 4/1932 | Friedman | 132/293 |
| D112,545 S | 12/1938 | Younghusband | |
| 2,171,112 A * | 8/1939 | Hoffman | 401/61 |
| 2,201,467 A | 5/1940 | Bloom | |
| D129,291 S | 9/1941 | Petzold | |
| D130,030 S | 10/1941 | Meyer | |
| 2,745,642 A * | 5/1956 | Hermann | 366/130 |
| D180,109 S | 4/1957 | Slater | |
| 2,998,896 A | 9/1961 | Miller | |
| 3,085,709 A | 4/1963 | Klein | |
| 3,292,840 A | 12/1966 | Schmidt | |
| 3,494,515 A | 2/1970 | Fattori | |
| D219,496 S | 12/1970 | Lebedeff | |
| 3,741,379 A * | 6/1973 | Kappler et al. | 206/457 |
| D230,954 S | 3/1974 | Gregorietti | |
| 3,843,120 A * | 10/1974 | Ricci | 473/2 |
| D240,711 S | 7/1976 | Angleman et al | |
| D243,585 S | 3/1977 | Angleman et al. | |
| 4,044,889 A | 8/1977 | Orentreich et al. | |

(Continued)

FOREIGN PATENT DOCUMENTS

| | | |
|---|---|---|
| JP | 2004106932 A | 4/2004 |
| KR | 20090006972 A | 1/2009 |

OTHER PUBLICATIONS

International Search Report for PCT/US2010/059025 dated Aug. 30, 2011.

(Continued)

*Primary Examiner* — David Walczak
*Assistant Examiner* — Jennifer C Chiang
(74) *Attorney, Agent, or Firm* — McCormick, Paulding & Huber LLP

(57) ABSTRACT

A lip balm applicator product comprises upper and lower portions that are connectable together to define the applicator product being of a substantially spherical shape. A support platform is located in the lower portion and accommodates a quantity of lip balm having an arcuate surface. A lip balm comprises a composition of waxes and oils in solid form and formed to have an arcuate surface. The composition is formed to have the arcuate surface using a hot pour process. A method of manufacturing a lip balm comprises providing a receptacle having a concave arcuate surface. A lip balm material in a heated, liquefied phase is poured into the receptacle. Once poured, the heated, liquefied phase is allowed to solidify such that a surface of the solidified lip balm material has an arcuate configuration that corresponds to the concave arcuate surface of the receptacle.

41 Claims, 4 Drawing Sheets

U.S. PATENT DOCUMENTS

| | | | |
|---|---|---|---|
| 4,124,135 A | 11/1978 | Weder et al. | |
| D253,394 S | 11/1979 | Berghahn et al. | |
| D255,653 S | 7/1980 | Lipsz | |
| D255,990 S | 7/1980 | Lucas | |
| D256,095 S | 7/1980 | Sandonato | |
| D258,199 S | 2/1981 | Torongo, Jr. | |
| D261,105 S | 10/1981 | Schwartz | |
| 4,342,522 A | 8/1982 | Mackles | |
| D266,146 S | 9/1982 | Morris | |
| D272,723 S | 2/1984 | Baker | |
| D273,766 S | 5/1984 | Lampe | |
| D280,289 S | 8/1985 | Aldrich, III et al. | |
| D286,616 S | 11/1986 | Becker | |
| 4,765,501 A | 8/1988 | Kao | |
| D317,118 S | 5/1991 | Crawford | |
| 5,025,817 A * | 6/1991 | Wen | 132/296 |
| 5,044,496 A * | 9/1991 | Tanaka et al. | 206/387.1 |
| D321,319 S | 11/1991 | Giuseppe | |
| 5,137,185 A * | 8/1992 | Mitchell | 222/390 |
| D333,780 S | 3/1993 | Jones et al. | |
| D333,784 S | 3/1993 | Goodman | |
| D339,986 S | 10/1993 | Garouste et al. | |
| D343,699 S | 1/1994 | Yang | |
| 5,287,979 A | 2/1994 | Bourgeois | |
| D346,112 S | 4/1994 | Alcindor | |
| D354,441 S | 1/1995 | Fontanella | |
| D357,584 S | 4/1995 | Swingler | |
| D368,220 S | 3/1996 | Bicknell et al. | |
| D368,427 S | 4/1996 | Bicknell et al. | |
| 5,503,825 A * | 4/1996 | Lane | 424/64 |
| 5,542,557 A * | 8/1996 | Koyama et al. | 215/347 |
| D377,757 S | 2/1997 | Bertolini et al. | |
| D387,662 S | 12/1997 | Bright et al. | |
| D389,409 S | 1/1998 | Tucker | |
| D393,421 S | 4/1998 | Kovens | |
| 5,743,404 A | 4/1998 | Melashenko et al. | |
| D398,533 S | 9/1998 | Kotyuk, Jr. et al. | |
| 5,808,215 A | 9/1998 | Kralik et al. | |
| D406,764 S | 3/1999 | Bright et al. | |
| D408,738 S | 4/1999 | Wu | |
| 5,925,391 A | 7/1999 | Whetstone, Jr. | |
| 5,988,424 A | 11/1999 | Kovens | |
| 6,010,264 A | 1/2000 | Scuderi et al. | |
| D422,904 S | 4/2000 | Lepsius et al. | |
| 6,050,438 A * | 4/2000 | Kovens et al. | 220/4.24 |
| 6,099,872 A | 8/2000 | Whetstone, Jr. | |
| 6,193,427 B1 * | 2/2001 | Benguigui | 401/88 |
| D443,726 S | 6/2001 | Faillant-Dumas | |
| 6,391,972 B1 * | 5/2002 | Hatakeyama | 525/191 |
| D458,835 S | 6/2002 | Delli-Venneri | |
| D459,216 S | 6/2002 | Heijdenrijk | |
| D465,733 S | 11/2002 | Hill | |
| D466,252 S | 11/2002 | Yu | |
| D476,884 S | 7/2003 | Miranda | |
| 6,626,313 B2 | 9/2003 | Herbstreit et al. | |
| D480,633 S | 10/2003 | Miranda | |
| 6,688,795 B1 * | 2/2004 | Jacob et al. | 401/207 |
| D489,148 S | 4/2004 | Sheng | |
| D504,979 S | 5/2005 | Lai | |
| D507,177 S | 7/2005 | Weissman | |
| D534,076 S | 12/2006 | Green et al. | |
| D554,529 S | 11/2007 | Green et al. | |
| D561,608 S | 2/2008 | Hogben | |
| D562,699 S | 2/2008 | Green et al. | |
| D564,900 S | 3/2008 | Green et al. | |
| D573,026 S | 7/2008 | Tsai | |
| D577,583 S | 9/2008 | Porter et al. | |
| D577,584 S | 9/2008 | Porter et al. | |
| D592,064 S | 5/2009 | Kilany | |
| D592,512 S | 5/2009 | Dubitsky et al. | |
| D598,608 S | 8/2009 | Baumer | |
| D602,663 S | 10/2009 | Pennington | |
| 7,631,781 B2 * | 12/2009 | Chen | 220/703 |
| D608,650 S | 1/2010 | Eisen | |
| D609,103 S | 2/2010 | Marold et al. | |
| D609,107 S | 2/2010 | Dubitsky et al. | |
| D610,458 S | 2/2010 | Martin | |
| D612,245 S * | 3/2010 | Canamasas Puigbo | D9/519 |
| D613,616 S | 4/2010 | Renz et al. | |
| 7,695,727 B2 * | 4/2010 | Magee et al. | 424/401 |
| D615,818 S | 5/2010 | Jansen | |
| D618,397 S | 6/2010 | Dubitsky et al. | |
| D618,398 S | 6/2010 | Dubitsky et al. | |
| D625,469 S * | 10/2010 | Dubitsky et al. | D28/84 |
| D631,204 S | 1/2011 | Dubitsky et al. | |
| D644,939 S * | 9/2011 | Teller | D9/726 |
| 2002/0008105 A1 | 1/2002 | Herbstreit et al. | |
| 2003/0201201 A1 * | 10/2003 | Cheng | 206/457 |
| 2004/0005186 A1 | 1/2004 | Ueda et al. | |
| 2006/0254945 A1 * | 11/2006 | Green et al. | 206/457 |
| 2007/0017915 A1 | 1/2007 | Weder et al. | |
| 2007/0108092 A1 | 5/2007 | Minuto et al. | |
| 2008/0019758 A1 | 1/2008 | Mallardi, III | |
| 2008/0110854 A1 | 5/2008 | Kelly | |
| 2008/0131187 A1 | 6/2008 | Breidenbach et al. | |
| 2011/0024316 A1 * | 2/2011 | Ginsburg | 206/385 |

OTHER PUBLICATIONS

Web page from www.amazon.com showing "Lancome Baume Baiser Hydrating Balm Sensual Massage for Lips" product and images (3 pages).

* cited by examiner

LIP BALM WITH SPHERICAL SURFACE AND METHOD FOR PRODUCING

TECHNICAL FIELD

The present invention relates to lip balms and, more particularly, a lip balm having a spherical surface and manufactured using a hot pour process.

BACKGROUND

Skin on and around the lips can often become chapped or otherwise damaged due to overexposure from elements such as sun and/or wind, particularly during athletic activities in which a person's face remains exposed to these elements for extended periods of time. The same skin can also become chapped or damaged while carrying out everyday non-athletic activities. For example, working outside in extreme cold, dry heat, or sun can also cause damage to the skin on the lips. Even working indoors or sleeping in dry conditions can cause the lips to chap, thereby leading to the development of cracks, which are often painful and can become infected.

Lip balms are often applied to prevent chapped lips. When applied prior to exposure to sun, wind, dry heat, or other extreme conditions, the lip balm can provide suitable protection to the skin on and around the lips. Even when applied after the skin on the lips is chapped, the lip balm can prevent any further damage from occurring. In either case, by providing a protective layer of lip balm, the risk of an infection developing in the damaged skin is minimized.

Lip balms are currently sold as emulsions, liquids, gels, or solids. In emulsion or liquid form, the lip balms are generally packed in containers such as jars. Gels (and liquids on occasion) are typically dispensed from squeeze tubes. Solid lip balms are generally packaged in stick form and dispensable from tubes or from lipstick-type applicators.

Solid lip balms are commonly manufactured using either a hot pour process or a bullet process. In the hot pour process, the lip balm ingredients are combined and heated in a liquefied phase. The liquid is then directly poured into the final consumer package, where it is cooled and solidifies. In the bullet process, the lip balm ingredients are also combined and heated in a liquefied phase. However, in the bullet process, the liquefied balm is poured into molds where it is cooled and solidified. The balm may then be cut into the desired shape and inserted into the consumer package.

The choice of the method used for a particular product depends on the design/functionality of the package, the additives in the balm, and the desired characteristics of the lip balm (color, feel, shape, and the like).

SUMMARY

In one aspect, the present invention resides in a lip balm applicator product that is substantially spherical in shape. The applicator product comprises upper and lower portions that are connectable together to define the substantially spherical shape of the applicator product. A support platform is located in the lower portion and accommodates a quantity of lip balm having an arcuate surface that can be exposed upon separation of the upper portion from the lower portion.

In another aspect, the present invention resides in a lip balm product comprising a composition of waxes and oils in solid form and formed to have an arcuate surface. The wax and oil composition can be eroded upon being drawn across a surface such as a user's lips. The composition is formed to have the arcuate surface using a hot pour process.

In another aspect, the present invention resides in a method of manufacturing a lip balm. In such a method, a receptacle having a concave arcuate surface is provided. A lip balm material in a heated, liquefied phase is also provided and poured into the receptacle. Once poured, the heated, liquefied phase is allowed to solidify such that a surface of the solidified lip balm material has an arcuate configuration that corresponds to the concave arcuate surface of the receptacle.

DETAILED DESCRIPTION

Figure 1:
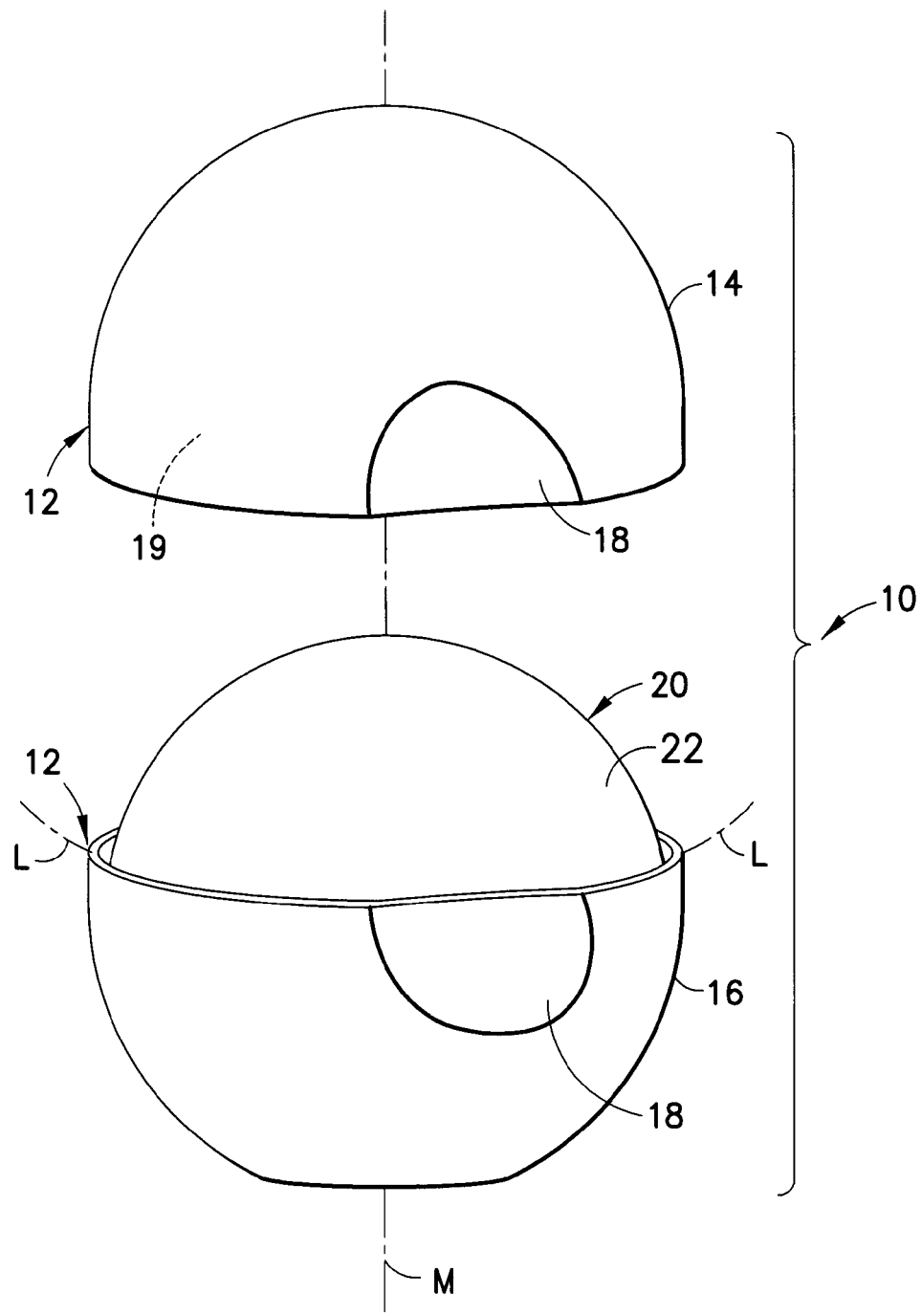
FIG. 1 is a perspective view of a lip balm applicator, of the present invention.

As is shown in FIG. 1, a lip balm applicator product having a lip balm composition is designated generally by the reference number 10 and is hereinafter referred to as "applicator 10." Applicator 10 comprises a receptacle 12 having the lip balm composition located therein. The receptacle 12 is substantially spherical in shape. The present invention is not limited in this regard, as the receptacle 12 may be substantially cylindrical with rounded surfaces, egg-shaped, ovate, or the like. The receptacle 12 comprises an upper portion 14 and a lower portion 16, the portions being separable from each other along a line L that extends substantially circumferentially about the receptacle perpendicular to a major axis M extending longitudinally through the receptacle. An interior surface 19 of the upper portion 14 of the receptacle 12 is defined by a concave surface having a spherical or arcuate topography. Although various surfaces described herein are referred to as being spherical, it should be understood that the term "spherical" includes arcuate surfaces.

The upper portion 14 and the lower portion 16 are connectable together via any suitable means such as the interengagement of threads. The present invention is not limited in this regard, as other mechanisms may be used to connect the upper portion 14 and the lower portion 16 together (e.g., engaging surfaces that fit together frictionally). The lip balm composition is located in the lower portion 16 and is hereinafter referred to as "lip balm 20."

The outer surface of the receptacle 12 includes a depression 18 formed partly on the upper portion 14 and partly on the lower portion 16. The depression 18 is a divot formed in the receptacle 12 that accommodates the thumb of a user to facilitate the opening and closing of the receptacle by alternatingly separating and connecting the upper portion 14 and the lower portion 16.

Upon separation of the upper portion 14 from the lower portion 16, the lip balm 20 is revealed. The lip balm 20 is mounted in the lower portion 16 on a support platform and is defined by a quantity of suitable lip balm material formed or otherwise configured to have a spherical shape that includes a spherical surface 22. The spherical shape and spherical surface 22 allows the lip balm material to extend above the upper edge of the lower portion 16, thereby facilitating the uninhibited application of the lip balm to a user's lips. The present invention is not limited to the lip balm 20 being configured to have a spherical shape and spherical surface 22, however, as other configurations are within the scope of the present invention.

Figure 2:
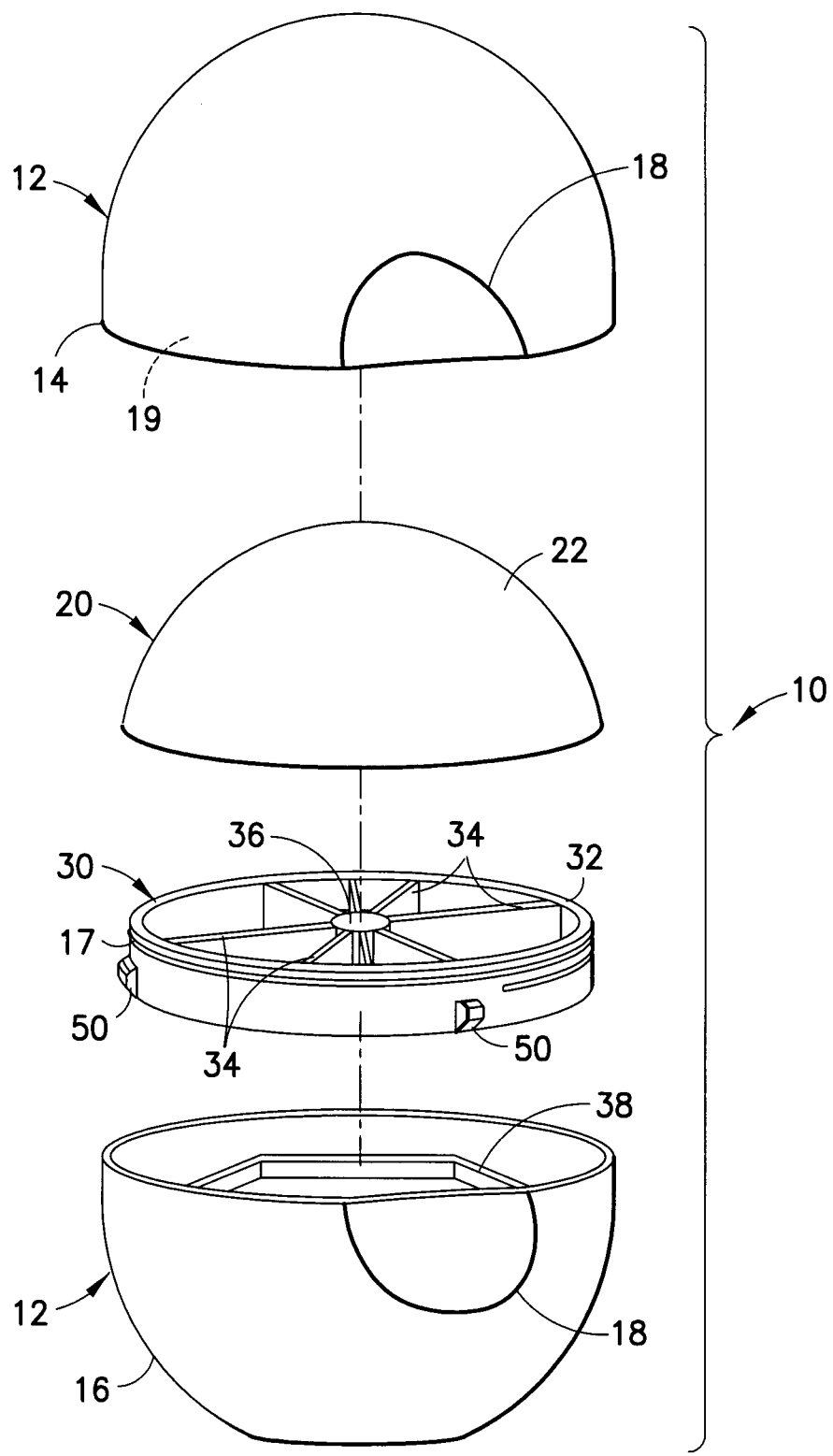
FIG. 2 is a perspective exploded view of the lip balm applicator of FIG. 1.

Referring now to FIG. 2, the support platform on which the lip balm 20 is mounted is designated generally by the reference number 30. The support platform 30 is a wheel having an outer rim 32 and threads 17 located thereon. A plurality of prongs 50 is located along a lower edge of the outer rim 32 (the edge opposite the threads 17) to facilitate the connection of the support platform 30 to an interior connecting structure such as ridges 38 in the interior of lower portion 16. In the assembly of the receptacle 10, the prongs 50 allow the support platform 30 to be snapplingly received on lower portion 16.

The support platform 30 includes a plurality of spokes 34 that extend from the outer rim 32 and that terminate at a hub 36. Both the widths of the spokes 34 and the diameter of the hub 36 are selected to provide a suitable area on which the lip balm 20 can be supported. The spokes 34 extend from the hub 36 at equal angles and connect with an inner surface of the outer rim 32. The present invention is not limited to the use of spokes and hubs, as the area bounded by the outer rim 32 can be solid. Although the outer rim 32 is described as being substantially circular, a portion along the edge of the outer rim is flattened to allow for the accommodation of the depression 18.

Figure 3:
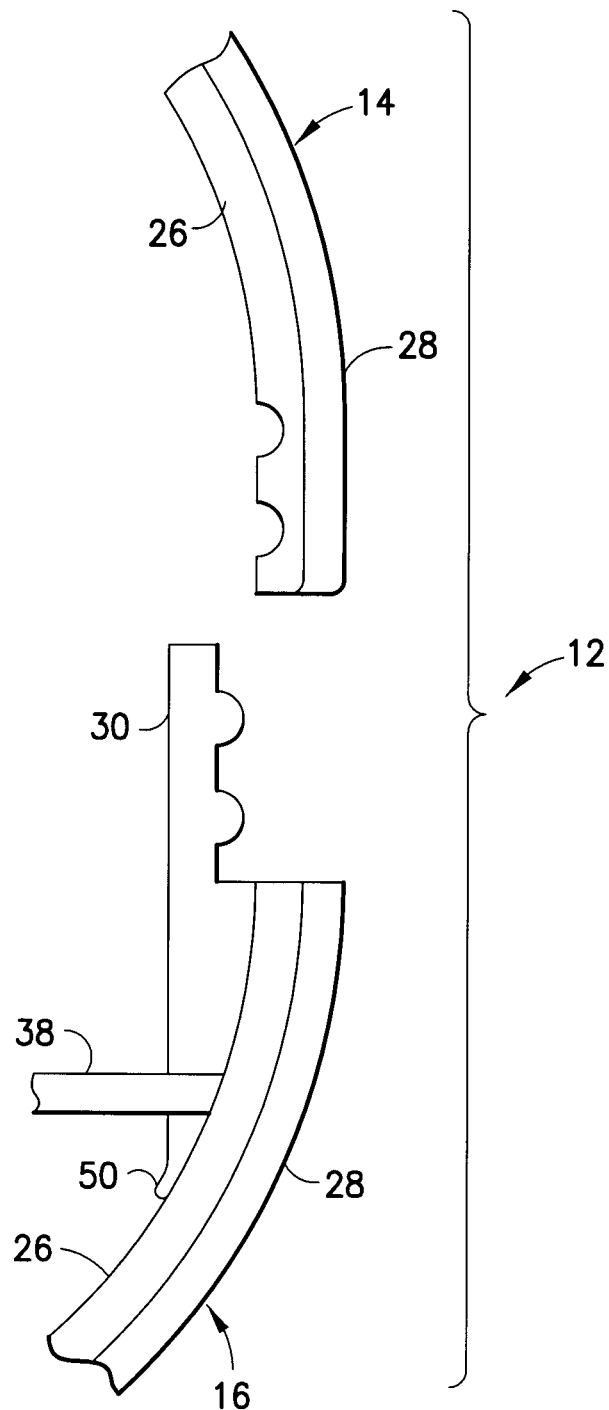
FIG. 3 is a schematic view of a portion of a receptacle of the lip balm applicator of FIG. 1.

Referring now to FIG. 3, both the upper portion 14 and the lower portion 16 of the receptacle 12 comprise a thermoplastic elastomer (TPE) injection molded over a plastic form comprising acrylonitrile-butadiene-styrene (ABS) copolymer. Accordingly, the defining surfaces of both the upper portion 14 and the lower portion 16 comprise a bottom layer 26 of ABS copolymer covered by a top layer 28 of TPE. The present invention is not limited to the bottom layer 26 being ABS copolymer, however, as the bottom layer in one or both of the upper portion 14 and the lower portion 16 can be polyethylene (PE). In such an alternate configuration, the tactile sensation to the user is slightly different upon handling the receptacle 12. In any configuration, the material of the top layer 28 provides a desirable tactile sensation to the user of the applicator 10, namely, by providing a soft surface that can be easily gripped, thereby facilitating the easy opening and closing of the receptacle 12.

The lip balm 20 comprises a quantity of suitable lip balm material. One exemplary lip balm material is a composition that is at least in part a blend of beeswax, coconut oil, olive oil, and jojoba oil that can be eroded when drawn over a surface (e.g., lips). The present invention is not limited to the lip balm material being a blend of such wax and oils, however, as other materials (e.g., petrolatum and petrolatum-based compounds) are within the scope of this disclosure. The blend of beeswax, coconut oil, olive oil, and jojoba oil can also include various ingredients including, but not limited to, emollients, ultraviolet protective agents, moisturizers, vitamins, aloe vera, colorants, fragrances, and the like. Drawing the material over a surface such as the lips causes the material to transfer to the surface as a film.

The spherical outer surface 22 of the lip balm 20 defines a mound-shaped quantity of the lip balm material. The spherical or mound shape provides desirable tactile sensations and use benefits as compared to stick (tubular) forms of the lip balm material. Desirable tactile sensations result from the spherical shape having a larger exposed surface area (as compared to the stick forms of the lip balm material) and the tactile sensation of a curved surface against the lips. Use benefits include the ability to apply the lip balm material to both lips simultaneously.

Figure 4:
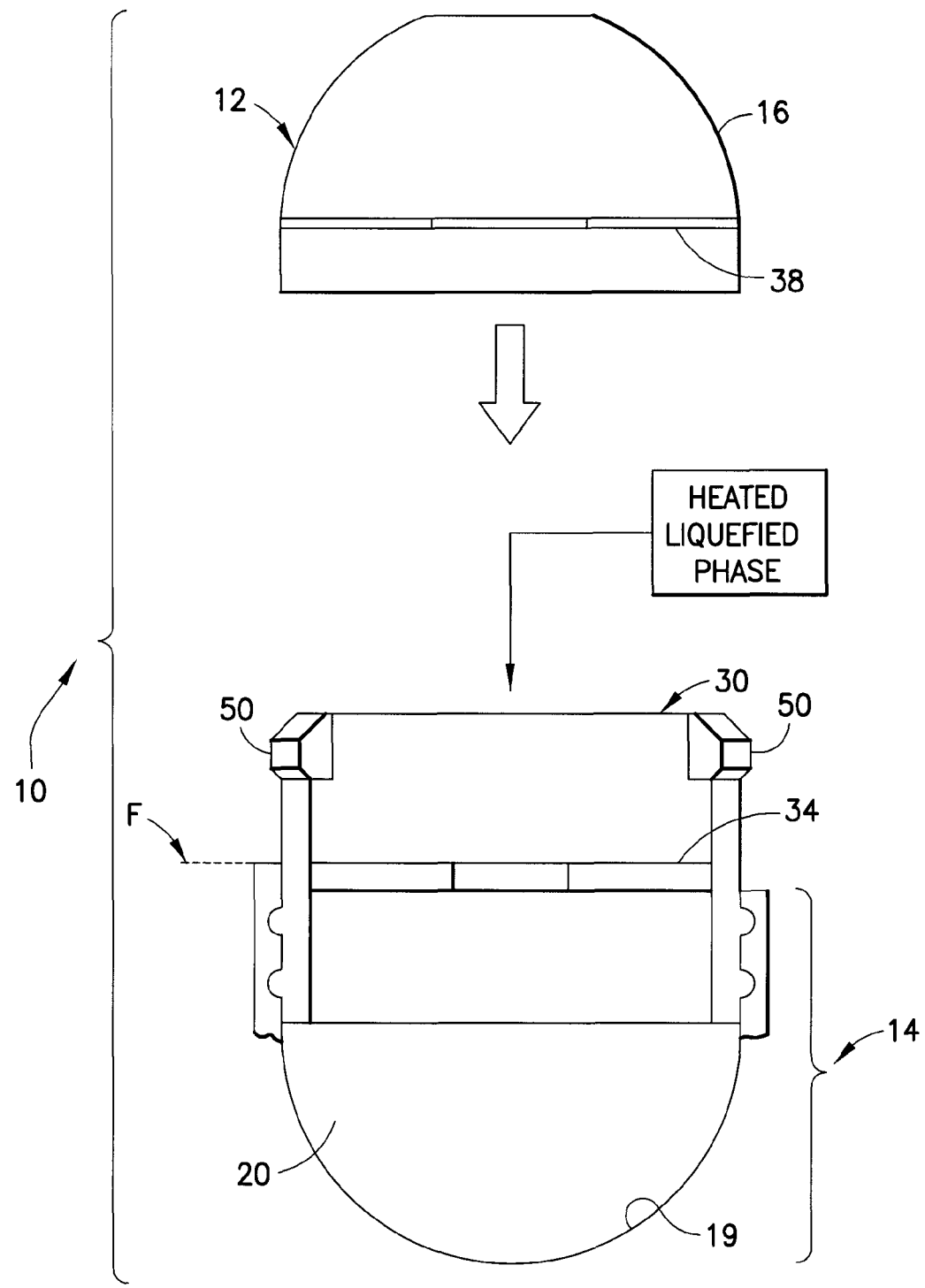
FIG. 4 is a schematic representation of a hot pour process of manufacturing a lip balm having an arcuate surface.

Referring now to FIG. 4, the lip balm 20 is manufactured from the lip balm material using a hot pour process. In using the hot pour process, the lip balm ingredients are combined and heated in a liquefied phase and poured into the final consumer packaging, which in this case is the receptacle 12. In preparation for the hot pour process, the support platform 30 is assembled with the upper portion 14 and inverted such that the support platform is level and vertical with regard to the upper portion. Orienting the assembled upper portion 14 and support platform 30 in this manner allows for the heated and liquefied phase to be poured into the upper portion and retained therein. The interior surface 19 of the upper portion 14 may be coated with a release agent prior to pouring the heated and liquefied phase, which thereby allows for efficient and clean removal of the upper portion by the user when using the finished product.

After the heated and liquefied phase is poured into the upper portion 14 and filled to a level F to cover at least a portion of the spokes 34, the liquefied phase is cooled or allowed to cool. The spokes 34 provide surfaces onto which the solidified lip balm material can adhere. The present invention is not limited to the solidification of the lip balm material around spokes, however, as the support platform can include any suitable configuration of surfaces around which the lip balm material can solidify. Upon sufficient solidification of the lip balm material, the lower portion 16 is inserted onto the assembled and filled upper portion 14 and support platform 30.

The use of the hot pour method in manufacturing the lip balm 20 defined by the spherical surface 22 provides cost benefits over similar methods that use the bullet method. In particular, using the hot pour method obviates the need for an intermediate step in which hot liquid is poured into separate molds, thereby also eliminating the need for additional equipment (molds). Furthermore, the additional steps of removing solidified product from molds and processing and handling the solidified product are avoided.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:
1. A lip balm applicator product comprising:
a substantially spherical receptacle including a lower portion having an upper end with an interior connecting structure and a lower end with a flat surface;
a support platform connectable with the interior connecting structure of the lower portion, the support platform having a wheel shape including:
an outer rim having an interior and an exterior with exposed threads along an upper portion of the exterior,
a central hub, and
a plurality of spokes extending from the interior of the outer rim and terminating at the hub;
an upper portion threadedly attachable to the support platform; and a lip balm mounted on the support platform, the lip balm having a substantially spherical upper surface that extends above the upper end of the lower portion.

2. The lip balm applicator product of claim 1, wherein the lip balm comprises petrolatum.

3. The lip balm applicator product of claim 2, wherein the lip balm comprises a colorant.

4. The lip balm applicator product of claim 3, wherein the lip balm comprises an ultraviolet protective agent.

5. The lip balm applicator product of claim 4, wherein the lip balm comprises a moisturizer.

6. The lip balm applicator product of claim 5, wherein the lip balm comprises a fragrance.

7. The lip balm applicator product of claim 6, wherein the lip balm comprises an emollient.

8. The lip balm applicator product of claim 7, wherein the lip balm comprises beeswax.

9. The lip balm applicator product of claim 7, wherein the lip balm comprises coconut oil.

10. The lip balm applicator product of claim 7, wherein the lip balm comprises olive oil.

11. The lip balm applicator product of claim 7, wherein the lip balm comprises jojoba oil.

12. The lip balm applicator product of claim 7, wherein the lip balm comprises aloe vera.

13. The lip balm applicator product of claim 7, wherein the lip balm comprises a vitamin.

14. The lip balm applicator product of claim 7, wherein the lower portion and the upper portion of the receptacle each include a cover layer of thermoplastic elastomer.

15. The lip balm applicator product of claim 7, wherein the lower portion and the upper portion comprise acrylonitrile-butadiene-styrene copolymer.

16. The lip balm applicator of claim 14, wherein the lower portion and the upper portion comprise polyethylene.

17. The lip balm applicator product of claim 14, further comprising a depression located on an outer surface of the receptacle, the depression being configured to accommodate the thumb of the user.

18. The lip balm applicator product of claim 1, further comprising a depression located on an outer surface of the receptacle, the depression being configured to accommodate the thumb of the user.

19. The lip balm applicator product of claim 1, wherein the lower portion and the upper portion of the receptacle each include a cover layer of thermoplastic elastomer.

20. The lip balm applicator product of claim 19, wherein the lower portion and the upper portion comprise acrylonitrile-butadiene-styrene copolymer.

21. The lip balm applicator of claim 19, wherein the lower portion and the upper portion comprise polyethylene.

22. The lip balm applicator product of claim 1, wherein the lip balm comprises beeswax.

23. The lip balm applicator product of claim 1, wherein the lip balm comprises coconut oil.

24. The lip balm applicator product of claim 1, wherein the lip balm comprises olive oil.

25. The lip balm applicator product of claim 1, wherein the lip balm comprises jojoba oil.

26. The lip balm applicator product of claim 1, wherein the lip balm comprises a blend of beeswax, coconut oil, olive oil, and jojoba oil.

27. The lip balm applicator product of claim 1, wherein the lip balm comprises aloe vera.

28. The lip balm applicator product of claim 1, wherein the lip balm comprises a colorant.

29. The lip balm applicator product of claim 1, wherein the lip balm comprises a moisturizer.

30. The lip balm applicator product of claim 1, wherein the lip balm comprises a fragrance.

31. The lip balm applicator product of claim 1, wherein the lip balm comprises an emollient.

32. The lip balm applicator product of claim 1, wherein the lip balm comprises an ultraviolet protective agent.

33. The lip balm applicator product of claim 1, wherein the lip balm comprises a vitamin.

34. A lip balm applicator product comprising:
   a receptacle including a lower portion having an upper end with an interior connecting structure;
   a support platform connectable with the interior connecting structure of the lower portion, the support platform having a wheel shape including:
      an outer rim having an interior and an exterior with exposed threads along an upper portion of the exterior,
      a central hub, and
      a plurality of spokes extending from the interior of the outer rim and terminating at the hub;
   an upper portion threadedly attachable to the support platform; and
   a lip balm mounted on the support platform, the lip balm having a substantially spherical upper surface.

35. The lip balm applicator product of claim 34, wherein the lip balm comprises petrolatum.

36. The lip balm applicator product of claim 35, wherein the lip balm comprises a colorant.

37. The lip balm applicator product of claim 36, wherein the lip balm comprises an ultraviolet protective agent.

38. The lip balm applicator product of claim 37, wherein the lip balm comprises a moisturizer.

39. The lip balm applicator product of claim 38, wherein the lower portion and the upper portion of the receptacle each include a cover layer of thermoplastic elastomer.

40. The lip balm applicator product of claim 39, wherein the lower portion and the upper portion comprise acrylonitrile-butadiene-styrene copolymer.

41. The lip balm applicator of claim 39, wherein the lower portion and the upper portion comprise polyethylene.

* * * * *